United States Patent
Srinivasan et al.

(10) Patent No.: US 11,020,540 B2
(45) Date of Patent: Jun. 1, 2021

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 221 days.

(21) Appl. No.: 16/094,382

(22) PCT Filed: Mar. 31, 2017

(86) PCT No.: PCT/US2017/025255
§ 371 (c)(1),
(2) Date: Oct. 17, 2018

(87) PCT Pub. No.: WO2017/189162
PCT Pub. Date: Nov. 2, 2017

(65) Prior Publication Data
US 2019/0167913 A1    Jun. 6, 2019

Related U.S. Application Data

(60) Provisional application No. 62/328,646, filed on Apr. 28, 2016.

(51) Int. Cl.
*A61M 5/34* (2006.01)
*A61B 5/15* (2006.01)
(Continued)

(52) U.S. Cl.
CPC ............ *A61M 5/345* (2013.01); *A61B 5/15* (2013.01); *A61M 5/00* (2013.01); *A61M 5/002* (2013.01);
(Continued)

(58) Field of Classification Search
CPC .......... A61M 2005/005; A61M 5/3297; A61M 5/3243–3275; A61M 5/15132;
(Continued)

(56) References Cited

U.S. PATENT DOCUMENTS 5,829,589 A    11/1998   Nguyen et al.
5,873,462 A    2/1999    Nguyen et al.
(Continued)

FOREIGN PATENT DOCUMENTS

EP    2119423 A1    11/2009
EP    2420270 A2    2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An attachable needle assembly (2) for use on a medication delivery pen (4), the needle assembly (2) comprising a spike housing (8) that is configured to engage the medication delivery pen (4) and pierce a reservoir septum (6) of the medication delivery pen (4), a needle assembly housing (22) secured to the spike housing (8), the needle assembly housing (22) enclosing a septum (40) with a cavity (42) that is in continuous fluid communication with the spike housing
(Continued)

(8), and a plurality of needles (44) configured to pierce the needle assembly septum (40), wherein when the needle assembly housing (22) is in a first position, the plurality of needles (44) are disengaged from the needle assembly septum (40), and when the needle assembly housing (22) is in a second position, one of the plurality of needles (46) enters into fluid communication with the septum cavity (42) and is exposed for medicament delivery.

20 Claims, 13 Drawing Sheets

(51) Int. Cl.
*A61M 5/00* (2006.01)
*A61M 5/31* (2006.01)
*A61M 5/24* (2006.01)
*A61M 5/32* (2006.01)

(52) U.S. Cl.
CPC ............... *A61M 5/24* (2013.01); *A61M 5/31* (2013.01); *A61M 5/32* (2013.01); *A61M 5/2466* (2013.01); *A61M 5/3202* (2013.01); *A61M 2005/004* (2013.01)

(58) Field of Classification Search
CPC .............. A61M 5/3295; A61M 5/3298; A61M 2005/004; A61M 5/002; A61M 5/24; A61M 5/31–3202; A61M 5/2466; A61M 5/345; A61M 5/15; A61M 5/00; A61M 5/3272; A61M 5/150496; A61M 5/15126–15132; A61M 5/15146–15163; A61M 2005/3208
See application file for complete search history.

(56) References Cited

U.S. PATENT DOCUMENTS

| | | |
|---|---|---|
| 5,931,817 A | 8/1999 | Nguyen et al. |
| 8,876,780 B2 | 11/2014 | Bruehwiler et al. |
| 9,101,724 B2 | 8/2015 | Chapin et al. |
| 9,107,988 B2 | 8/2015 | Bruehwiler et al. |
| 9,155,838 B2 | 10/2015 | Bilton et al. |
| 9,381,303 B2 | 7/2016 | Abhijitsinh et al. |
| 9,717,860 B2 | 8/2017 | Bruehwiler et al. |
| 10,029,042 B2 | 7/2018 | Searle et al. |
| 2001/0014792 A1 | 8/2001 | West et al. |
| 2002/0020646 A1 | 2/2002 | Groth et al. |
| 2002/0020647 A1 | 2/2002 | Groth |
| 2005/0084631 A1 | 4/2005 | Anderson |
| 2008/0312604 A1 | 12/2008 | Boesen |
| 2010/0217206 A1 | 8/2010 | Lum et al. |
| 2011/0068034 A1 | 3/2011 | Hwang et al. |
| 2012/0004620 A1 | 1/2012 | Spool et al. |
| 2012/0016315 A1 | 1/2012 | Radmer et al. |
| 2012/0041373 A1* | 2/2012 | Bruehwiler ........... A61M 5/002 604/173 |
| 2012/0041381 A1 | 2/2012 | Raj et al. |
| 2012/0041383 A1* | 2/2012 | Bruehwiler ........... A61M 5/008 604/192 |
| 2012/0041390 A1 | 2/2012 | Spool et al. |
| 2013/0041321 A1* | 2/2013 | Cross .................. A61M 5/2448 604/189 |
| 2013/0053751 A1 | 2/2013 | Holtham |
| 2014/0076758 A1 | 3/2014 | Dasbach et al. |
| 2014/0123479 A1 | 5/2014 | Dasbach |
| 2014/0262884 A1 | 9/2014 | Priebe et al. |
| 2014/0299622 A1 | 10/2014 | Hofmann et al. |
| 2014/0332425 A1 | 11/2014 | Hofmann et al. |
| 2014/0339113 A1 | 11/2014 | Hofmann et al. |
| 2015/0025469 A1* | 1/2015 | Larsen ................. A61M 5/002 604/173 |
| 2015/0163898 A1 | 6/2015 | Mokhtarzad |
| 2015/0283333 A1 | 10/2015 | Butler et al. |
| 2015/0335827 A1 | 11/2015 | Stefansen et al. |
| 2015/0346184 A1 | 12/2015 | Galasso |
| 2016/0000992 A1 | 1/2016 | Steel et al. |
| 2016/0030683 A1 | 2/2016 | Taylor et al. |
| 2016/0074587 A1 | 3/2016 | Searle et al. |
| 2016/0082195 A1 | 3/2016 | Atterbury et al. |
| 2016/0106925 A1 | 4/2016 | Boesen |

FOREIGN PATENT DOCUMENTS

| | | |
|---|---|---|
| EP | 2428236 A1 | 3/2012 |
| EP | 2586475 A1 | 5/2013 |
| EP | 2604304 A | 6/2013 |
| EP | 2696913 B1 | 9/2015 |
| WO | 2008/150715 A1 | 12/2008 |
| WO | WO-2011083055 A1 | 7/2011 |
| WO | 2014/020001 A1 | 2/2014 |
| WO | 2016/050902 A1 | 4/2016 |

* cited by examiner

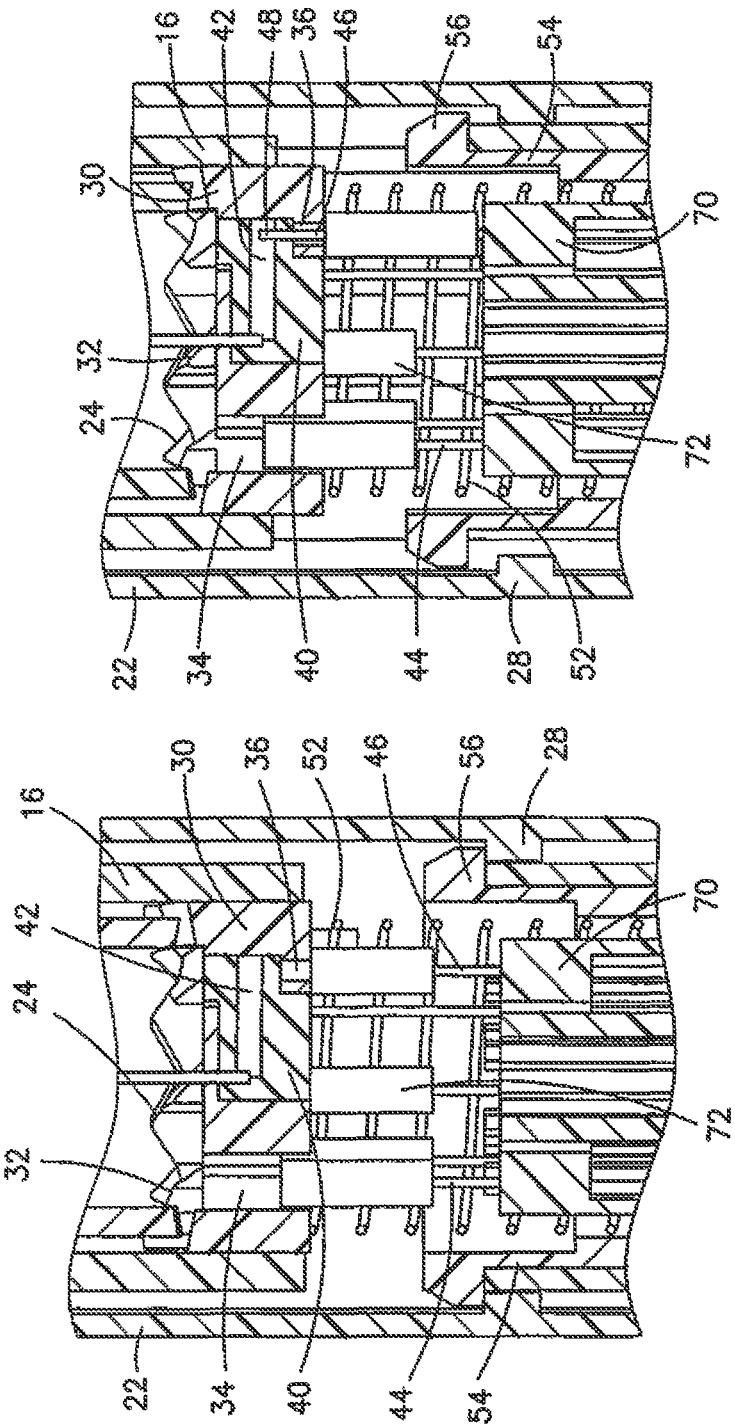

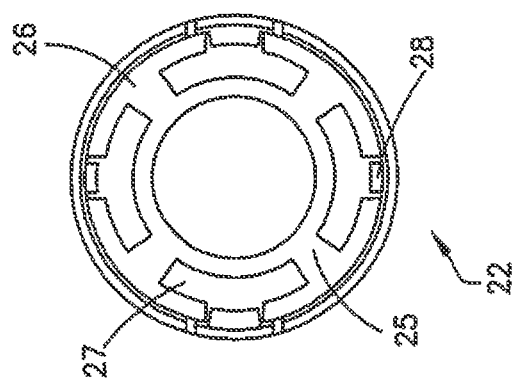
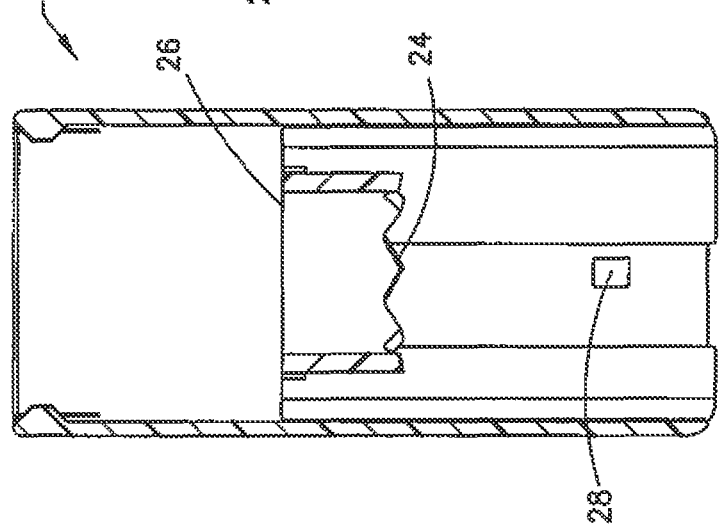
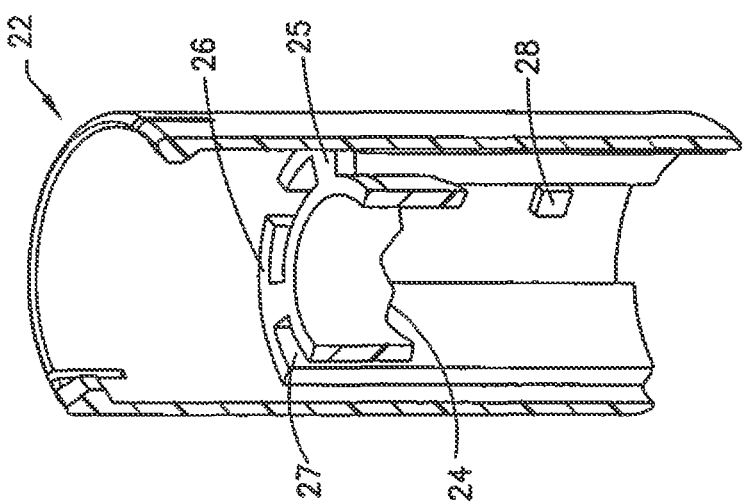

PEN NEEDLE MAGAZINE

This application claims the benefit under 35 U.S.C. § 119(e) of U.S. Provisional Patent Application Ser. 62/328,646, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication delivery pen to provide a magazine of needles for use. Such a needle assembly provides advantages in separating a patient end and a non-patient end and allows for engagement and disengagement to the medication delivery pen. Moreover, improvements in sterility, simplicity and safety are achieved by the needle assembly such that none of the needles in the magazine pierce a vial, cartridge or a reservoir septum of the medication delivery pen during operation, the plurality of needles only move axially and do not substantially move radially and do not substantially rotate, and the needles are unable to be reused.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a spike housing that is configured to engage the medication delivery pen and pierce a vial, cartridge or a reservoir septum of the medication delivery pen, a needle assembly housing secured to the spike housing, the needle assembly housing enclosing a needle assembly septum having a septum cavity, the septum cavity being in continuous fluid communication with the spike housing, and a plurality of needles configured to pierce the needle assembly septum, wherein when the needle assembly housing is in a first position, the plurality of needles are disengaged from the needle assembly septum, and when the needle assembly housing is in a second position, one of the plurality of needles enters into fluid communication with the septum cavity and is exposed for medicament delivery.

The foregoing and/or other aspects of the present invention can also be achieved by a method of operating an attachable needle assembly for a medication delivery pen, the method comprising securing the medication delivery pen to a spike housing, piercing a vial, cartridge or a reservoir septum of the medication delivery pen by the spike housing, the spike housing secured by a needle assembly housing, and establishing fluid communication between a septum cavity of a needle assembly septum and the spike housing, wherein when the needle assembly housing is in a first position, the plurality of needles are disengaged from the needle assembly septum, and when the needle assembly housing is in a second position, one of the plurality of needles enters into fluid communication with the septum cavity and is exposed for medicament delivery.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 6 illustrates a partial cross sectional view of the rotating ratchet contacting one of a plurality of needles;

FIG. 7 illustrates a partial cross sectional view of the rotating ratchet engaging one of a plurality of needles;

FIG. 12A illustrates a left side perspective partial cross sectional view of a needle assembly housing;

FIG. 12B illustrates a front cross sectional view of the needle assembly housing;

FIG. 12C illustrates a top elevation view of the needle assembly housing;

FIG. 5 illustrates a left perspective view of a needle assembly septum;

DETAILED DESCRIPTION OF EXEMPLARY EMBODIMENTS

Figure 1:
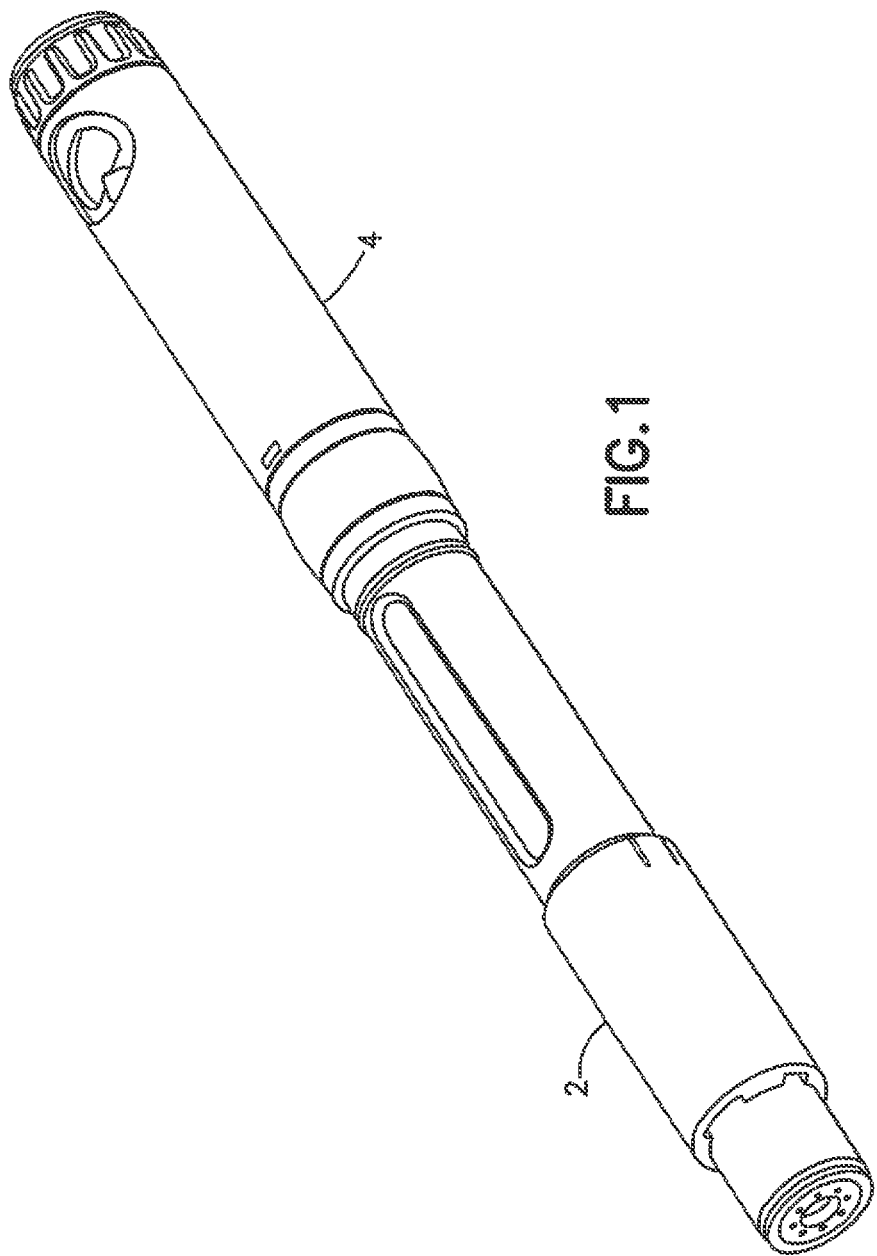
FIG. 1 illustrates a right side perspective view of an exemplary medication delivery pen connected to a needle assembly.
Figure 2:
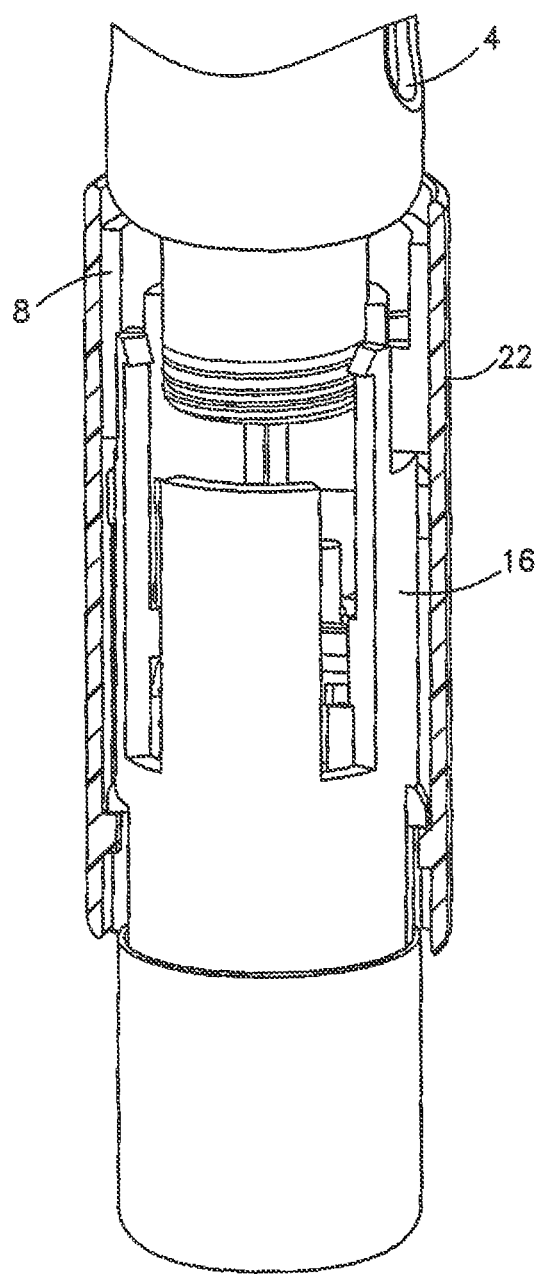
FIG. 2 illustrates a partial cross sectional view of the medication delivery pen connected to the needle assembly.

FIG. 1 illustrates a medication delivery pen 4 used for injecting medicament, such as liquid drugs, into a living body. The needle assembly 2 is mounted on the medication delivery pen 4 to enhance medication delivery. According to one embodiment, FIG. 2 illustrates the needle assembly 2 including a spike housing 8 that threadably engages the medication delivery pen 4, although other forms of engagement are contemplated. Benefits and advantages of the needle assembly 2 are described below.

Figure 3:
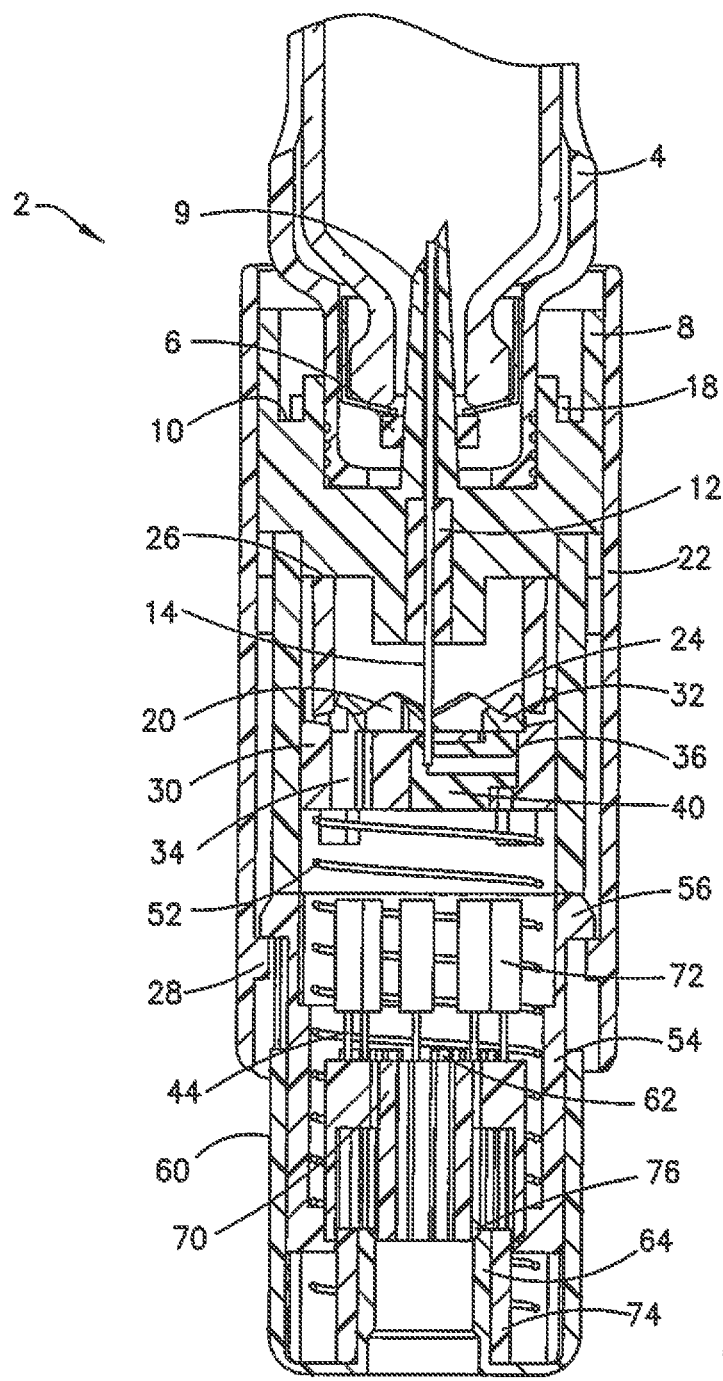
FIG. 3 illustrates a cross sectional view of a first position of the needle assembly.

According to one embodiment, FIG. 3 illustrates a cross sectional view of a first position of the needle assembly 2 where none of a plurality of needles 44 are exposed for medicament delivery. The needle assembly 2 preferably includes a magazine of needles 44. The plurality of needles 44 includes eight hollow needles, although more or less needles are contemplated.

Figure 13:
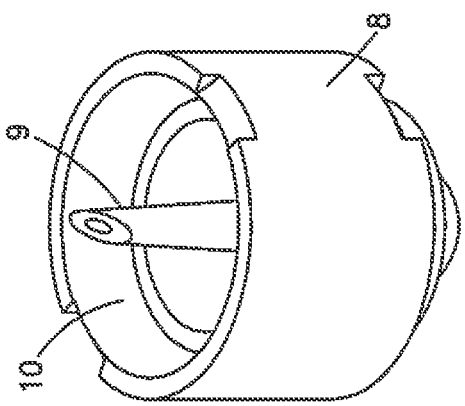
FIG. 13 illustrates a front perspective view of a spike housing.

The needle assembly 2 includes the spike housing 8 that is also illustrated in FIG. 13. The spike housing 8 includes a hollow spike 9, spike openings 10 and a spike septum 12. The hollow spike 9 is configured to pierce a vial, cartridge or a reservoir septum 6 of the medication delivery pen 4 to establish fluid communication with the needle assembly 2. When the reservoir septum 6 is pierced, medicament travels through the hollow spike 9. The spike openings 10 are configured to engage a main housing 16 to secure the spike housing 8 to the needle assembly 2. The spike septum 12 is disposed at a bottom portion of the spike housing 8 and cooperates with the hollow spike 9 to regulate the flow of medicament to and from the spike housing 8.

Figure 14:
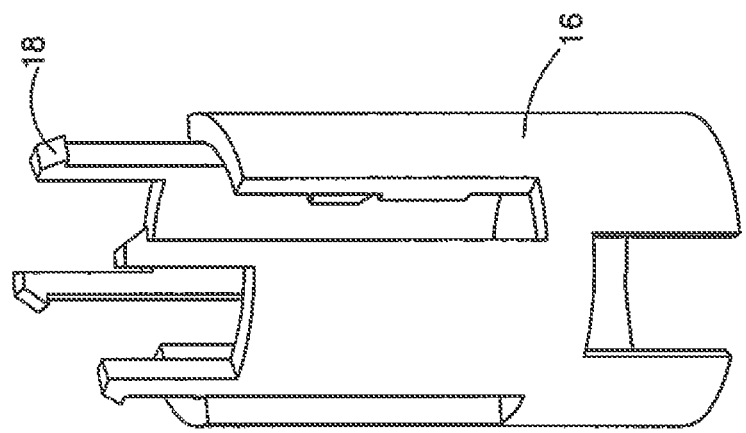
FIG. 14 illustrates a right side perspective view of a main housing.

According to one embodiment, the main housing 16 is disposed in a needle assembly housing 22 but the needle assembly housing 22 is configured to move axially relative to the main housing 16. As illustrated in FIG. 14, the main housing 16 includes flanges 18 that are received by the spike openings 10. The flanges 18 and the spike openings 10 secure the main housing 16 to the spike housing 8. The main housing 16 of FIG. 3 also includes a first curvilinear path 20. The first curvilinear path 20 includes a series of protrusions having a plurality of vertical and angled surfaces that define a particular path via. Operation of the first curvilinear path 20 in the needle assembly 2 is further described below.

FIG. 3 illustrates that the spike housing 8 is disposed in the needle assembly housing 22. The needle assembly housing 22, according to one embodiment illustrated in FIGS. 12A-12C, encloses the main components of the needle assembly 2. The needle assembly housing 22 includes a second curvilinear path 24. The second curvilinear path 24 includes a plurality of pointed or triangular shaped teeth having angled surfaces in between each tooth. The second curvilinear path 24 cooperates with the first curvilinear path 20 of the main housing 16 for operation of the needle assembly 2. The needle assembly housing 22 also includes a mounting surface 26 that engages the bottom surface of the spike housing 8, and an inner wall 28 that contacts a needle retriever 54. An inner flange 25 connects the inner diameter of the needle assembly housing 22 to the second curvilinear path 24. A plurality of hollow cavities 27 is disposed between portions of the inner flange 25. The plurality of cavities 27 allows the needle assembly housing 22 to move axially relative to the main housing 16. However, the needle assembly housing 22 does not rotate relative to the main housing 16. Specifically, each pair of flanges 18 of the main housing 16 is disposed in each respective cavity 27 of the needle assembly housing 22. These features are further described in detail below.

Figure 15:
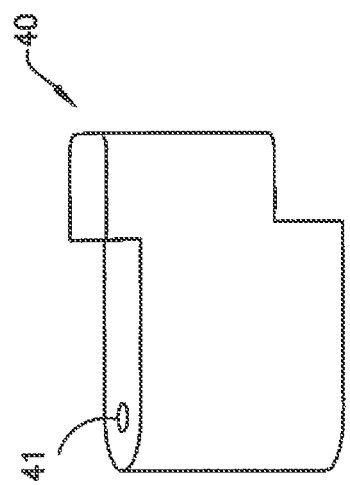

The needle assembly housing 22 of FIG. 3 further encloses a needle assembly septum 40 which is disposed in a rotating ratchet 30. According to one embodiment, FIG. 15 illustrates the needle assembly septum 40 which includes a hole 41 for establishing fluid communication with the hollow spike 9. The needle assembly septum 40 also includes a longitudinal septum cavity 42 (or septum cavity) as illustrated in FIGS. 6 and 7 for the purpose of distributing medicament.

Figure 16:
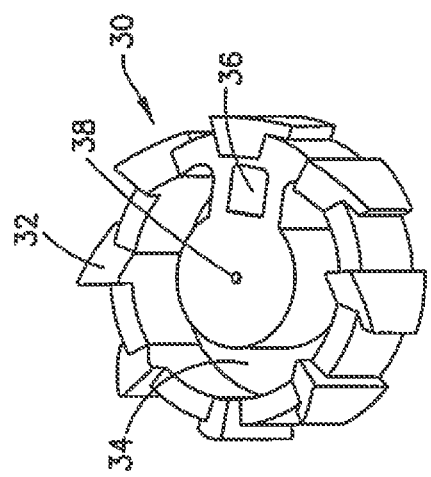
FIG. 16 illustrates a front perspective view of the rotating ratchet.

According to one embodiment, the needle assembly septum 40 is disposed in a cavity 36 of the rotating ratchet 30. The rotating ratchet 30, as illustrated in FIG. 16, also includes a follower 32, a hollow opening 34 and a ratchet hole 38. The follower 32 includes a plurality of pointed or triangular shaped teeth having angled surfaces in between the teeth. The follower 32 engages and travels along the first and second curvilinear paths 20, 24 to rotate the rotating ratchet 30 during axial movement of the needle assembly housing 22 between the first position and a second position. In other words, the first and second curvilinear paths 20, 24 guide the follower 32 of the rotating ratchet 30 to selectively rotate. The hollow opening 34 provides an area for a plurality of needles 44 to enter during operation when one of the plurality of needles 44 is engaged with the needle assembly septum 40. Finally, the ratchet hole 38 is configured to establish fluid communication between the needle assembly septum 40 and the hollow spike 9 by a fluid communication needle 14.

Specifically, according to one embodiment, the fluid communication needle 14 is bonded or fixed to the ratchet hole 38 of the rotating ratchet 30. A distal end of the fluid communication needle 14 is fixedly positioned to be in fluid communication with the longitudinal septum cavity 42. During assembly, the fluid communication needle 14 enters the ratchet hole 38, the spike septum 12 and the hollow spike 9 so that a proximal end of the fluid communication needle 14 is in fluid communication with the medication delivery pen 4. The fluid communication needle 14 moves axially through the spike septum 12 and along with the rotating ratchet 30 and the needle assembly housing 22 when the needle assembly 2 travels between the first and second positions.

The plurality of needles 44, according to one embodiment, is configured to pierce the needle assembly septum 40. When the plurality of needles 44 is in the first position of the needle assembly 2, none of the needles pierce the needle assembly septum 40. In the second position of the needle assembly 2, only one needle of the plurality of needles 44 pierces the needle assembly septum 40 at a single time. Accordingly, a remaining plurality of needles 44 enters into the hollow opening 34 of the rotating ratchet 30 when the one needle pierces the needle assembly septum 40.

Figure 17:
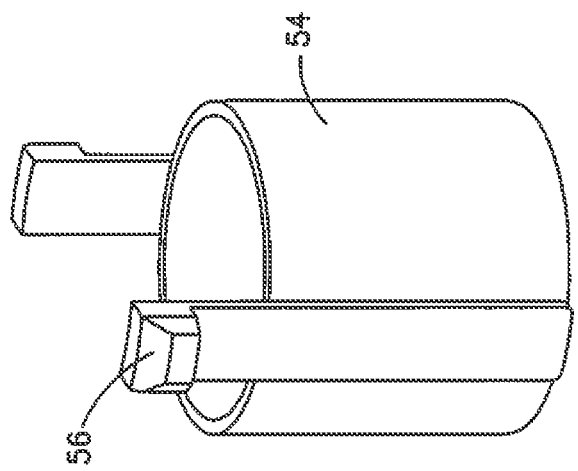
FIG. 17 illustrates a right side perspective view of a needle retriever.

The needle assembly 2 of FIG. 3 further includes a spring 52 and the needle retriever 54 that surround the plurality of needles 44. The needle retriever 54, as further illustrated in FIG. 17, includes flanges 56 that contact the inner wall 28 of the needle assembly housing 22 to compress the spring 52 in the first position of the needle assembly 2. When the needle assembly 2 is in the second position, the needle retriever 54 cooperates with the spring 52 to move the needle assembly 2 back to the first position.

In the first position of the needle assembly 2, the spring 52 is compressed between a bottom surface of the rotating ratchet 30 where the needle assembly septum 40 is disposed and a bottom interior surface of the needle retriever 54. A top surface of the needle retriever 54 contacts a bottom surface of the main housing 16 to place the spring 52 in a compressed state in the first position of the needle assembly 2. Specifically, the portion of the needle assembly housing 22 at the second curvilinear path 24 forcibly contacts the bottom surface of the spike housing 8 because of the compressed spring 52. The rotating ratchet 30 also forcibly contacts the first curvilinear path 20 because of the compressed spring 52. The first curvilinear path 20 is fixed in the first position of the needle assembly 2 via the spike housing 8 being secured to the main housing 16 as described above. The first curvilinear path 20 does not move between the first and second positions of the needle assembly 2, whereas the needle assembly housing 22 travels between the first and second positions of the needle assembly 2.

Figure 18:
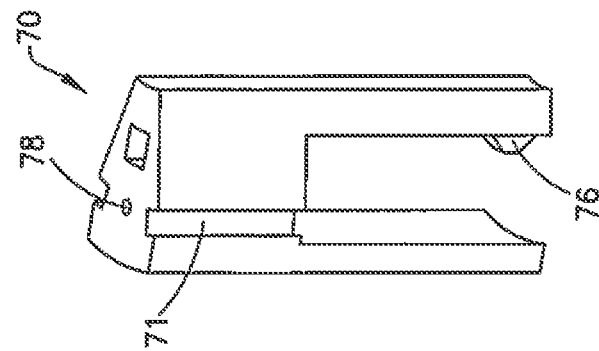
FIG. 18 illustrates a right side perspective view of a needle post.
Figure 20:
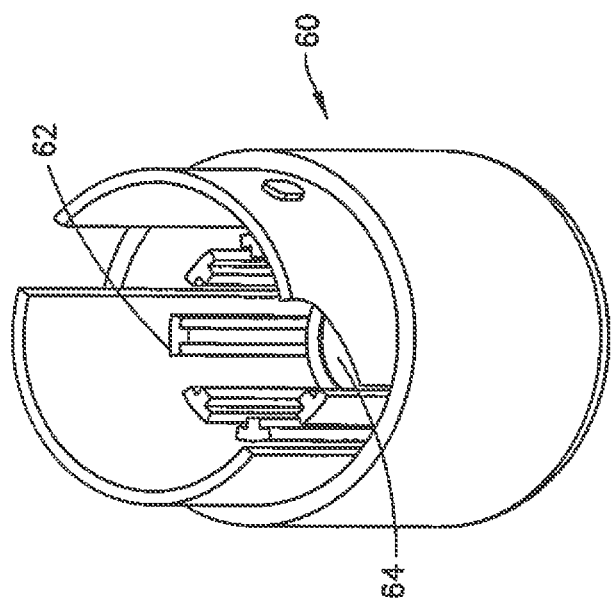
FIG. 20 illustrates a front perspective view of a needle housing.

The plurality of needles 44 is disposed in the needle retriever 54. Specifically, according to one embodiment, each of the plurality of needles 44 is fixed to a needle post 70 via a needle hole 78 as illustrated in FIG. 18. The needle post 70 of FIG. 18 is illustrated in an original state and is configured to elastically deflect when the needle assembly 2 moves between the first and second positions. The needle post 70 further includes side cavities 71 and a projection 76. The side cavities 71 engage with needle housing protrusions 62 of a needle housing 60 to secure each of the needle posts 70. The needle housing 60 is further illustrated in FIG. 20. The projection 76 locks the needle post 70 in each of a top position and a bottom position with respect to an inner diameter 64 of the needle housing 60 when the needle assembly 2 moves between the first and second positions. All needle posts 70 are in the original state in both of the top and bottom positions. However, the needle post 70 of the one needle of the plurality of needles 44 elastically deflects when moving between the top and bottom positions. During assembly, the needle housing 60 is secured to the main housing 16 via snaps, a Luer ultrasonic welding or adhesives, for example. A bottom surface of the plurality of needle posts 70 rests on the bottom inner surface of the needle retriever 54.

Figure 19:
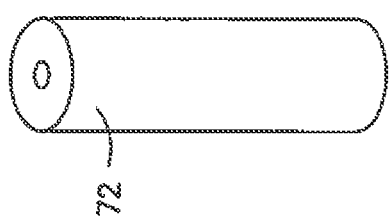
FIG. 19 illustrates a right side perspective view of a first sterility barrier.

According to one embodiment, each of the plurality of needles 44 includes a first sterility barrier 72 at a proximal end of the needle 44 and a second sterility barrier 74 at a sharpened distal end of the needle 44. The first sterility barrier 72 is illustrated in FIG. 19. The plurality of second sterility barriers 74 is disposed at a bottom inner surface of the needle housing 60, and along an outer surface of the inner diameter 64 of the needle housing 60. The sterility barriers 72, 74 are composed of, for example, a soft non-coring elastomer such as silicone, isoprene or butyl.

In the first position of the needle assembly 2, all of the plurality of needles 44 is protected and sterilized by the first and second sterility barriers 72, 74. Additionally, in the first position of the needle assembly 2, the plurality of first sterility barriers 72 is assembled on each of the plurality of needles 44 with a gap between a bottom surface of the plurality of first sterility barriers 72 and a top surface of the plurality of needle posts 70. On the other hand, a top surface of each of the plurality of second sterility barriers 74 contacts the bottom surface of the plurality of needle posts 70, and a bottom surface of the plurality of needle posts 70 contacts the bottom inner surface of the needle housing 60.

Operation of the needle assembly 2 is described as follows. As iterated above, FIG. 3 illustrates the first position of the needle assembly 2. Due to the compression of the spring 52, the first position of the needle assembly 2 places the needle assembly housing 22 in a compressed state. A user pulls the needle assembly housing 22 away from the medication delivery pen 4 to move the needle assembly 2 from the first position to the second position.

Figure 4:
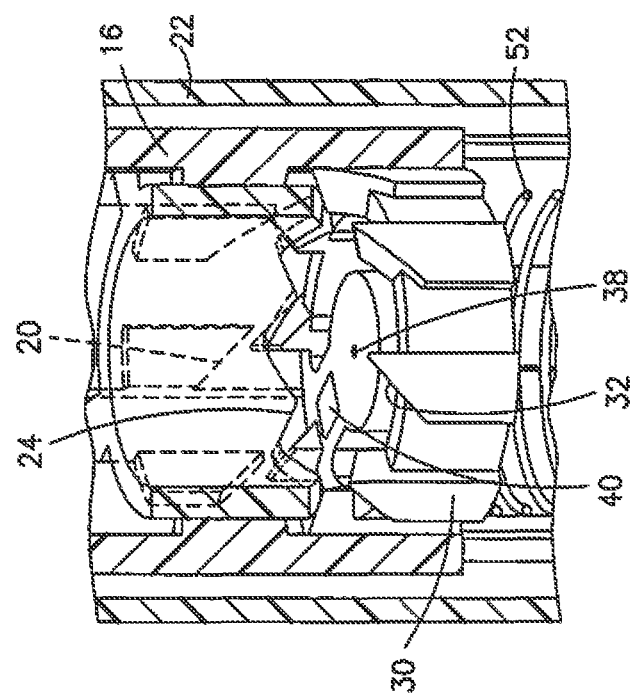
FIG. 4 illustrates a partial cross sectional view of a rotating ratchet traveling from the first position to a second position of the needle assembly.

FIG. 4 illustrates the user pulling the needle assembly housing 22 downward toward the second position of the needle assembly 2. During this point in operation of the needle assembly 2, the second curvilinear path 24 of the needle assembly housing 22 also moves downward to further compress the spring 52. The follower 32 of the rotating ratchet 30 is pushed downward by the second curvilinear path 24 of the needle assembly housing 22 and travels along the first curvilinear path 20 of the main housing 16.

Figure 5:
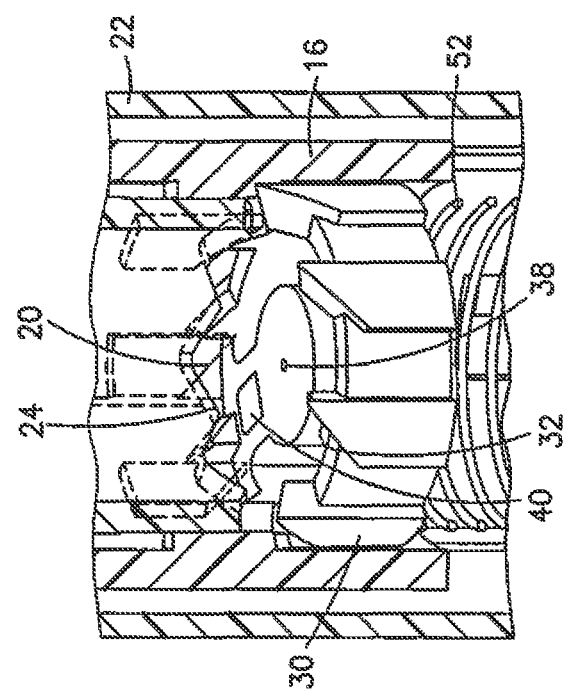
FIG. 5 illustrates a partial cross sectional view of the rotating ratchet traveling from the first position to the second position of the needle assembly.

FIG. 5 illustrates the rotating ratchet 30 continuing downward toward the second position of the needle assembly 2. As the rotating ratchet 30 moves downward, the spring 52 is compressed and applies a counteracting upward axial force. After the follower 32 of the rotating ratchet 30 exits the first curvilinear path 20 of the main housing 16, the rotating ratchet 30 continues to rotate since the follower 32 is guided along the second curvilinear path 24 of the needle assembly housing 22. The upward axial force from the spring 52 ensures that the rotating ratchet 30 continues to contact and be guided by the first and second curvilinear paths 20, 24. The first and second curvilinear paths 20, 24 are advantageously arranged to be partially offset with respect to each other. This offset causes the additional rotation of the rotating ratchet 30 as the follower 32 transitions and travels from the first curvilinear path 20 to the second curvilinear path 24. The offset is configured so that the follower 32 is predominately guided and traveling along one of the first and second curvilinear paths 20, 24.

FIG. 6 illustrates the follower 32 of the rotating ratchet 30 reaching a stopping point along the second curvilinear path 24. At this time, the rotating ratchet 30 is aligned for engagement with a selected needle 46 of the plurality of needles 44. The rotating ratchet 30 continues to move downward until the bottom surface of the rotating ratchet 30 contacts the first sterility barrier 72 of the selected needle 46. The remaining needles of the plurality of needles 44 do not contact the bottom surface of the rotating ratchet 30. Instead, the remaining needles of the plurality of needles 44 are aligned with the hollow opening 34 of the rotating ratchet 30.

FIG. 7 illustrates the rotating ratchet 30 continuing to move downward toward the second position of the needle assembly 2. A proximal end 48 of the selected needle 46 pierces the first sterility barrier 72 and is exposed. Specifically, the bottom surface of the rotating ratchet 30 contacts an outside circumferential portion of a top surface of the first sterility barrier 72. As the rotating ratchet 30 moves downward, the first sterility barrier 72 of the selected needle 46 also moves downward and the proximal end 48 of the selected needle 46 pierces through the top surface of the first sterility barrier 72.

The proximal end 48 of the selected needle 46 travels into the cavity 36 of the rotating ratchet 30 where the needle assembly septum 40 is disposed. Specifically, the proximal end 48 of the selected needle 46 pierces the needle assembly septum 40 and establishes fluid communication with the longitudinal septum cavity 42 of the needle assembly septum 40. When the proximal end 48 of the selected needle 46 pierces the needle assembly septum 40, the remaining needles of the plurality of needles 44 and their respective first sterility barriers 72 enter further into the hollow opening 34 of the rotating ratchet 30. Additionally, when the proximal end 48 of the selected needle 46 pierces the needle assembly septum 40, a bottom surface of the first sterility barrier 72 of the selected needle 46 contacts the top surface of the respective needle post 70.

Figure 8:
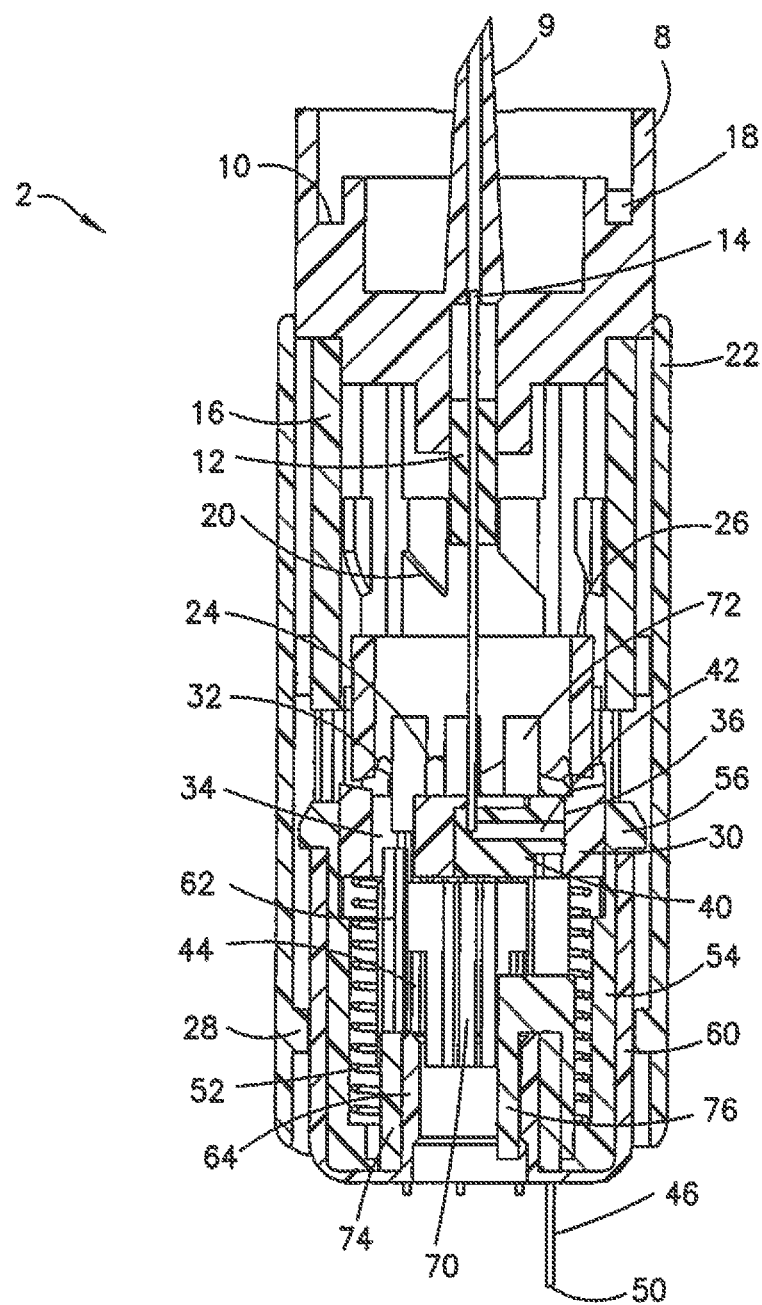
FIG. 8 illustrates a cross sectional view of the second position of the needle assembly.

FIG. 8 illustrates the second position of the needle assembly 2. When the needle assembly housing 22 enters into the second position of the needle assembly 2, the rotating ratchet 30 and the first sterility barrier 72 of the selected needle 46 moves the respective needle post 70 from the top position to the bottom position. Moving the needle post 70 of the selected needle 46 to the bottom position causes a distal end 50 of the selected needle 46 to pierce the respective second sterility barrier 74. The distal end 50 of the selected needle 46 is now exposed for medication delivery.

At the top position, the needle post 70 of the selected needle 46 is snap locked to the inner diameter 64 of the needle housing 60 via the projection 76 in the first position of the needle assembly 2. When the needle post 70 of the selected needle 46 travels downward to the bottom position, the needle post 70 slides along the side cavities 71 that engage the needle housing protrusions 62. The projection 76 elastically deflects and disengages from the inner diameter 64. When the needle assembly 2 is in the second position, the needle post 70 of the selected needle 46 elastically deflects back to its original state in the bottom position and engages the inner diameter 64 again.

The needle posts 70 of the remaining plurality of needles 44 do not move and instead stay in the top position. This is because the plurality of first sterility barriers 72 of each of the remaining plurality of needles 44 extends further into the hollow opening 34 of the rotating ratchet 30. The remaining plurality of needles 44 does not pierce each of the respective second plurality of sterility barrier 74. Thus, the remaining plurality of needles 74 continues to be sealed and sterilized by both the first and second plurality of sterility barriers 72, 74.

The user is unable to move the needle assembly 2 beyond the second position because the needle assembly housing 22 will not be able to move down any further. Specifically, this is because the second curvilinear path 24 of the needle assembly housing 22 contacts the follower 32 of the rotating ratchet 30 and the bottom surface of the rotating ratchet 30 contacts the first sterility barrier 72 of the selected needle 46. The bottom surface of the first sterility barrier 72 of the selected needle 46 contacts the needle post 70 of the selected needle 46 and the bottom surface of the needle post 70 of the selected needle 46 contacts the bottom inner surface of the needle retainer 54. Finally, a bottom outer surface of the needle retainer 54 contacts the bottom inner surface of the needle housing 60 thus creating a defined and fixed movement path. The spring 52 is in the most compressed state when the needle assembly 2 is in the second position.

FIG. 8 further illustrates that, as the rotating ratchet 30 moves downward, the fluid communication needle 14 simultaneously moves downward because the fluid communication needle 14 is fixed to the needle assembly septum 40. Although the fluid communication needle 14 moves downward, the spike septum 12 remains pierced so that fluid communication between the needle assembly septum 40 and the hollow spike 9 is maintained. Accordingly, the second position of the needle assembly 2 allows medicament to be delivered from the medication delivery pen 4 to the distal end 50 of the selected needle 46.

When the user releases the needle assembly housing 22, the needle assembly 2 begins to move from the second position back to the first position. The spring 52 is released which causes the rotating ratchet 30 and the second curvilinear path 24 of the needle assembly housing 22 to move upward and toward the medication delivery pen 4.

Figure 9:
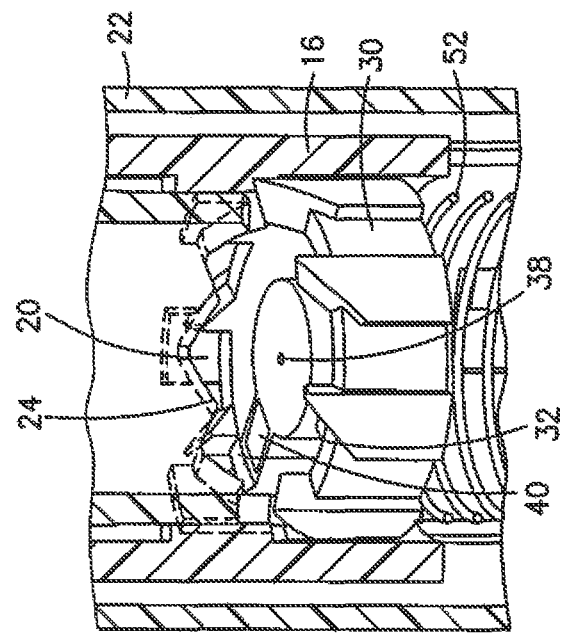
FIG. 9 illustrates a partial cross sectional view of the rotating ratchet traveling from the second position to the first position of the needle assembly.
Figure 10:
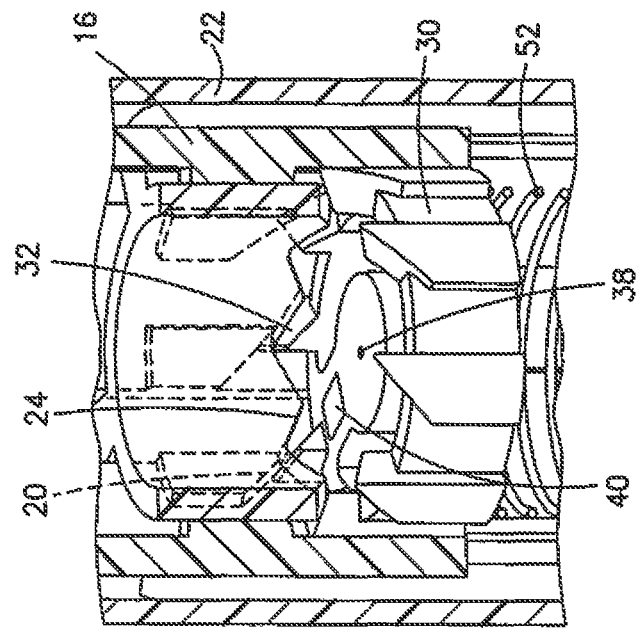
FIG. 10 illustrates a partial cross sectional view of the rotating ratchet traveling from the second position to the first position of the needle assembly.

FIGS. 9 and 10 illustrate how the rotating ratchet 30 moves axially and rotates as the needle assembly 2 returns to the first position. Specifically, the follower 32 of the rotating ratchet 30 engages the angled surface of the first curvilinear path 20 of the main housing 16 to move upward and rotate. After the follower 32 travels beyond the first curvilinear path 20, the follower 32 transitions and engages the second curvilinear path 24 of the needle assembly housing 22 and continues to rotate until it contacts another portion of the first curvilinear path 20 (FIG. 10). As described above, the upward axial force from the spring 52 ensures that the rotating ratchet 30 continues to contact and be guided by the first and second curvilinear paths 20, 24. The first and second curvilinear paths 20, 24 are offset to provide the continuous rotation and axial movement of the rotating ratchet 30.

The rotating ratchet 30 subsequently continues to move upward until the mounting surface 26 of the needle assembly housing 22 contacts the bottom surface of the spike housing 8. The rotating ratchet 30 has now rotated a specific angle but is not yet aligned to an adjacent needle of the plurality of needles 44. The rotating ratchet 30 will only be aligned to the adjacent needle when the needle assembly 2 moves again to the first position.

Figure 11:
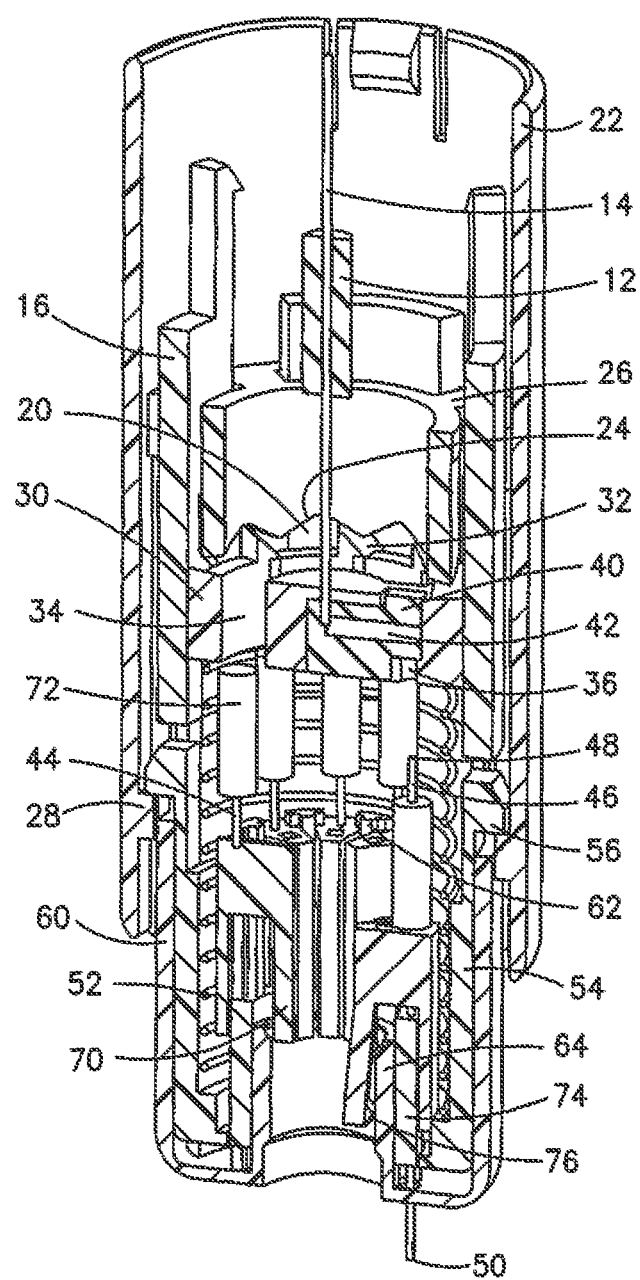
FIG. 11 illustrates a cross sectional view of the needle assembly traveling from the second position to the first position.

FIG. 11 illustrates the needle assembly 2 in the process of returning to the first position from the second position. As the needle assembly housing 22 returns to the first position of the needle assembly 2, the inner wall 28 of the needle assembly housing 22 contacts the flange 56 of the needle retriever 54. This contact causes the needle assembly housing 22 to pull the needle retriever 54 upward. The spring force 52 is greater than the frictional forces of the needle assembly 2 in the second position to cause the needle assembly 2 to return back to the first position.

When the needle retriever 54 moves upward, the needle post 70 of the selected needle 46 moves upward from the bottom position and toward the top position. The needle post 70 moves to the top position because the bottom surface of the needle post 70 contacts the bottom inner surface of the needle retriever 54. The side cavities 71 of the needle post 70 travel upward along the respective needle housing protrusion 62. The projection 78 of the needle post 70 will disengage from the inner diameter 64 of the needle housing 60 via elastic deformation and travel upward. Subsequently, the projection 78 of the needle post 70 engages a top portion of the inner diameter 64 of the needle housing 60 in the first position of the needle assembly 2. Since the selected needle 46 is fixed to the needle post 70, the selected needle 46 will also move upward. The distal end 50 of the selected needle 46 will reenter the second sterility barrier 74 and protect the user from inadvertent operation.

Figure 12:
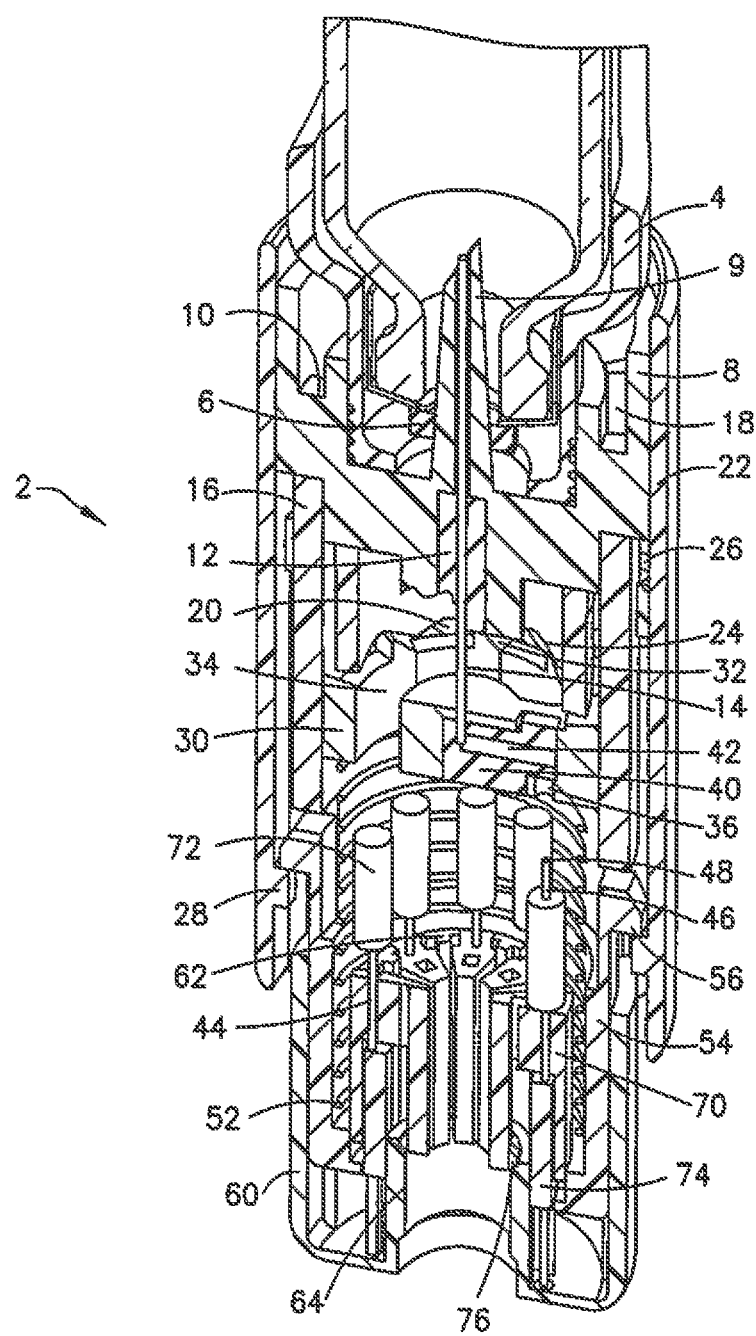
FIG. 12 illustrates a cross sectional view of the needle assembly returning to the first position.

FIG. 12 illustrates the needle assembly 2 back in the first position. The proximal end 48 of the selected needle 46 is still exposed but it is contained within the needle assembly housing 22. The first sterility barrier 72 of the selected needle 46 still contacts the top surface of the needle post 70 but this does not affect the normal operation of the needle assembly 2.

The fluid communication needle 14 also moves when the needle assembly 2 returns from the second position to the first position. Since the fluid communication needle 14 is fixed to the needle assembly septum 40 disposed in the rotating ratchet 30, the fluid communication needle 14 also moves upward and continues to maintain fluid communication between the hollow spike 9 and the needle assembly septum 40.

The process of moving between the first and second positions repeats so that each of the plurality of needles 44 of the needle assembly 2 is used. In other words, the selected needle changes based on the alignment of the needle assembly septum 40 in the rotating ratchet 30. The selected needle alternates to an adjacent needle of the plurality of needles 44 based on the rotation of the rotating ratchet 30. Accordingly, when each selected needle engages the needle assembly septum 40, the remainder of the plurality of needles 44 enters into the hollow opening 34 of the rotating ratchet 30.

The first and second curvilinear paths 20, 24 are configured such that no needle is selected after the last needle of the plurality of needles 44 is used. In other words, when the rotating ratchet 30 rotates after use of the last needle of the plurality of needles 44, the first and second curvilinear paths 20, 24 are configured not to rotate the rotating ratchet 30 any further. Specifically, the rotating ratchet 30 stops on the last needle because no curvilinear path 20 exists for the last needle. Thus, the last needle is reusable, while the remaining plurality of needles 44 is configured for a single use and not reusable. Alternatively, the rotating ratchet 30 locks the last needle in place by rotating the rotating ratchet 30 half its normal distance so that the last needle and the first needle are both not engaged.

During operation, the plurality of needles 44 does not substantially move radially. Rather, the needle assembly housing 22 moves axially to engage and move the selected needle 46 of the plurality of needles 44 each time the needle assembly 2 enters into the second position. Such a design advantageously simplifies the assembly, improves robustness and increases reliability. No substantial radial or rotational movement in this regard is understood as 0±5% with respect to a center axis of the needle assembly 2. Preferably, one skilled in the art understands that substantial in this context means that no radial of rotational movement is required to perform the intended function. Slight radial or rotational movement is desired to ensure the proper spacing of parts for smooth operation and proper movement of the needles axially without jamming.

Each of the plurality of needles 44 is advantageously isolated from the reservoir septum 6 of the medication delivery pen 4 throughout the operation of the needle assembly 2. That is, none of the plurality of needles 44 pierces the reservoir septum 6 of the medication delivery pen 4 at any point during the operation of the needle assembly 2. Such an arrangement advantageously provides simplicity in design, improves sterility and provides a separation between a patient end and a non-patient end.

Figure 21:
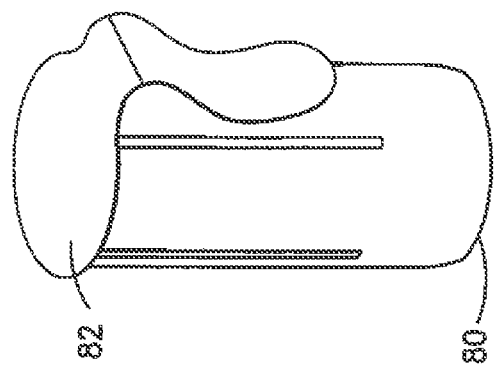
FIG. 21 illustrates a right side perspective view of a cover and teardrop label enclosing the needle assembly.

According to one embodiment, FIG. 21 illustrates the cover 80 enclosing the needle assembly 2. The cover 80 is sealed with a teardrop label 82 to seal the needle assembly 2 and maintain its sterility for transportation and security purposes prior to operating with the medication delivery pen 4. When the needle assembly 2 is ready for use, the user peels off the teardrop label 82 and removes the needle assembly 2 from the cover 80.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
   a needle assembly housing that moves between a first position and a second position, the needle assembly housing surrounding:
      a rotating ratchet that includes a needle assembly septum having a septum cavity; and
      a plurality of needles configured to open the needle assembly septum,
   wherein
   when the needle assembly housing is in the first position, the plurality of needles are disengaged from the needle assembly septum, and when the needle assembly housing is in the second position, one of the plurality of needles enters into fluid communication with the septum cavity and is exposed for medicament delivery; and
   when the needle assembly housing moves from the first positon to the second position, the rotating ratchet rotates to align the septum cavity with one of the plurality of needles.

2. The attachable needle assembly of claim 1, further comprising
   a spring applying a compression force to the needle assembly septum, wherein
   when the needle assembly housing is released from the second position, the spring returns the needle assembly housing to the first position.

3. The attachable needle assembly of claim 2, further comprising
a needle retriever including a flange, the needle retriever surrounding the plurality of needles, wherein
the spring causes the flange to contact the needle assembly housing in the first position to maintain constant compression of the spring.

4. The attachable needle assembly of claim 1, further comprising
a main housing disposed in the needle assembly housing, the main housing including a first curvilinear path, wherein
the rotating ratchet includes a follower comprised of angled surfaces; and
the follower travels along the first curvilinear path to rotate the rotating ratchet as the needle assembly housing is moved between the first position and the second position so that a different needle of the plurality of needles opens the septum cavity each time the needle assembly housing is in the second position.

5. The attachable needle assembly of claim 4, wherein the needle assembly housing moves axially relative to the main housing.

6. The attachable needle assembly of claim 4, wherein the needle assembly housing includes a second curvilinear path that cooperates with the first curvilinear path and guides the follower of the rotating ratchet to rotate.

7. The attachable needle assembly of claim 1, wherein when the needle assembly housing is in the second position, a remainder of the plurality of needles enters into a hollow opening in the rotating ratchet.

8. The attachable needle assembly of claim 1, wherein when the one needle of the plurality of needles returns from the second position to the first position, the one needle of the plurality of needles is unable to be reused.

9. The attachable needle assembly of claim 1, further comprising
a plurality of needle posts that each secures one of the plurality of needles; and
a needle housing that stores each of the plurality of needle posts, wherein
the plurality of needle posts is engaged to the needle housing in the first and second positions of the needle assembly housing.

10. The attachable needle assembly of claim 1, wherein
each needle of the plurality of needles is secured in a respective needle post, and
when the needle assembly housing moves from the first position to the second position, the needle post of the one needle moves from a top position to a bottom position in a needle housing to expose the one needle for medicament delivery.

11. The attachable needle assembly of claim 10, wherein when the needle assembly housing moves from the first position to the second position, a remainder of the plurality of needles extends further into a hollow opening of the rotating ratchet.

12. The attachable needle assembly of claim 1, wherein
a proximal end of the plurality of needles is each enclosed by a first sterility boot when the needle assembly housing is in the first position, wherein
when the needle assembly housing is in the second position, the first sterility boot of the one needle of the plurality of needles is opened to establish fluid communication between the one needle and the septum cavity of the needle assembly septum.

13. The attachable needle assembly of claim 1, wherein
a distal end of the plurality of needles is each enclosed by a second sterility boot when the needle assembly housing is in the first position, wherein
when the needle assembly housing is in the second position, the second sterility boot of the one needle of the plurality of needles is opened to expose the one needle for medicament delivery.

14. The attachable needle assembly of claim 13, wherein each second sterility boot lies at a bottom interior surface of a needle housing.

15. The attachable needle assembly of claim 1, wherein the plurality of needles does not open a reservoir septum of the medication delivery pen.

16. The attachable needle assembly of claim 1, wherein the plurality of needles does not substantially rotate or substantially move radially.

17. The attachable needle assembly of claim 1, wherein the plurality of needles includes eight needles.

18. The attachable needle assembly of claim 1, wherein the needle assembly housing moves from the first position to the second position by traveling away from the medication delivery pen.

19. The attachable needle assembly of claim 1, further including
a cover enclosing the needle assembly; and
a label sealing the needle assembly in the cover and maintaining sterility prior to operating with the medication delivery pen.

20. A method of operating an attachable needle assembly on a medication delivery pen, the needle assembly comprising a needle assembly housing surrounding (1) a rotating ratchet including a needle assembly septum having a septum cavity and (2) a plurality of needles configured to open the needle assembly septum, the method comprising:
moving the needle assembly housing from a first position to a second position;
rotating the rotating ratchet to align one of the plurality of needles to the septum cavity;
establishing fluid communication between the septum cavity and the one of the plurality of needles for medicament delivery;
moving the needle assembly housing from the second position to the first position;
ending fluid communication between the septum cavity and the one of the plurality of needles; and
rotating the rotating ratchet to begin aligning a subsequent needle of the plurality of needles to the septum cavity.

* * * * *